United States Patent [19]

Crandall et al.

[11] 4,315,505
[45] Feb. 16, 1982

[54] TRACHEOSTOMY TUBE WITH DISPOSABLE INNER CANNULA

[75] Inventors: Norman C. Crandall, Costa Mesa; Robert C. French, El Toro, both of Calif.

[73] Assignee: Shiley, Inc., Irvine, Calif.

[21] Appl. No.: 137,626

[22] Filed: Apr. 7, 1980

[51] Int. Cl.$^3$ ............................................. A61M 25/02
[52] U.S. Cl. ........................... 128/200.26; 128/207.15
[58] Field of Search .............. 128/200.26, 136, 202.28, 128/207.14, 207.15, 207.16, 207.17, 348, 349 R, 349 B

[56] References Cited

U.S. PATENT DOCUMENTS

| | | | |
|---|---|---|---|
| 2,765,792 | 10/1956 | Nichols | 128/200.26 |
| 3,606,669 | 9/1971 | Kemble | 128/200.26 |
| 4,009,720 | 3/1977 | Crandall | 128/207.15 |
| 4,033,353 | 7/1977 | La Rosa | 128/207.15 |

*Primary Examiner*—Henry J. Recla
*Attorney, Agent, or Firm*—Knobbe, Martens

[57] ABSTRACT

A tracheostomy tube includes an outer cannula and a removable, disposable inner cannula. The inner cannula is provided with a tapered portion located just behind its distal tip which forms simultaneously an air tight seal with the outer cannula and a stop device for preventing the protrusion of the tip substantially beyond the end of the outer cannula. The stop device furthermore compensates for variations in the length of the inner cannula by controlling the position of the tip between a location flush with the end of the outer cannula and one just slightly beyond. A coupling connector is mounted on the proximal end of the inner cannula to provide easy, releasable attachment of the inner cannula to the outer cannula. The inner cannulae are inexpensively constructed from a soft, flexible polyvinyl chloride material and are dimensionally compatible with any particular outer cannula.

4 Claims, 4 Drawing Figures

TRACHEOSTOMY TUBE WITH DISPOSABLE INNER CANNULA

RELATED APPLICATION

The present application is the parent application of a continuation in part application, Ser. No. 260,072, filed May 4, 1981.

BACKGROUND OF THE INVENTION

The present invention relates to tracheostomy tubes having an outer cannula and a removable inner cannula, and, in particular, to a tracheostomy tube having a disposable inner cannula.

Tracheostomy tubes have been used for some time to provide a bypass supply of air or mixture of gases to a patient having an obstruction in the larynx or the pharynx areas of the throat. The distal end of the tracheostomy tube is inserted into the trachea through an incision in the patient's neck below the obstructed area. The proximal end of the tube remains outside the trachea in communication with ambient air to permit passage of such air into the trachea. This proximal end of the tube can also be attached to a respiratory device to assist the patient's breathing or to anesthesia equipment for passing anesthetic gas to the patient prior to surgery.

While thus in place within the patient's trachea, a tracheostomy tube can sometimes become partially or completely obstructed by accumulations of mucus or completely obstructed by accumulations of mucus or phlegm. U.S. Pat. No. 3,693,624 to Shiley et al, assigned to Shiley, Inc., assignee of the present invention, discloses and claims a tracheostomy tube which allows such obstructions to be cleared without causing pain and irritation to the patient, this invention providing an outer cannula, which remains in place in the trachea, and a removable inner cannula, which serves as an inner lining of the outer cannula. Thus, to clear the passageway of the tracheostomy tube, the inner cannula can be removed, cleaned, and then replaced.

An important feature of lined tracheostomy tubes, which insures adequate cleaning, is that the inner cannula runs the entire length of the outer cannula. For example, if the distal tip of the inner cannula were to terminate within the bore of the outer cannula, mucus could accumulate on and adhere to the unlined portion of the interior surface of the outer cannula, obstructing the air passage of the tube and requiring its complete removal for cleaning. At the same time, however, the inner cannula should not extend substantially beyond the outer cannula, since removal and insertion of a protruding inner cannula could cause abrasion of the trachea and damage to the delicate cilia along the inner tracheal wall. Thus, the overall length of such removable inner cannulae must be carefully controlled.

It is also important in such two-part, lined tracheostomy tubes that an adequate air seal be maintained between the inner and outer cannulae so that respiration pressure from an artificial respiration machine is not lost by leakage. One prior method for producing such an air seal at the proximal end of a tracheostomy tube is disclosed in U.S. Pat. No. 4,009,720 to Crandall, entitled "Wedge Seal for a Tracheotomy Tube" assigned to Shiley, Inc.

SUMMARY OF THE INVENTION

The tracheostomy tube of the present invention provides a disposable inner cannula, so that the time and expense associated with cleaning and sterilizing it can be eliminated. A significant feature of this invention is that each disposable inner cannula is dimensionally compatible with any particular outer cannula of the same type and size, while at the same time possessing the critical length and air seal characteristics mentioned above. Furthermore, the inner cannula is sufficiently inexpensive to manufacture to make disposability practical, and yet dimensional tolerances may be held sufficiently close to achieve interchangeability.

In the present invention a tapered distal portion on the inner cannula provides both an air seal with the outer cannula and a stop device for preventing the substantial protrusion of the inner cannula beyond the distal end of the outer cannula. Thus, the stop device compensates for variations in length among the present inner cannulae and maintains their dimensional compatibility with the outer cannulae.

The tapered surface on the inner cannula faces and is located just behind the extreme distal tip of the inner cannula. The angle of inclination of the tapered surface is such that its diameter, at least at one point, is greater than the inside diameter of the narrowed distal end of the outer cannula. Thus, pressing the inner cannula longitudinally into the bore of the outer cannula will result in a tight, wedged engagement between the two to form the air seal and stop devices.

The stop device on the inner cannula is designed so that the inner cannula tip is flush with or extends only slightly beyond the end of the outer cannula. Thus, the position of the tip, regardless of the length of the inner cannula, is controlled or regulated to fall within this narrow range. In order to prevent irritation to the trachea, should it be contacted by the tip of the inner cannula, the tip is rounded. Furthermore, the inner cannula is constructed from a soft, biologically inactive polyvinyl chloride material, further protecting the patient's trachea. This material is also very flexible to permit the inner cannula of the present invention to bend within the outer cannula.

The inner cannula is removably attached to the outer cannula by means of a coupling connector which advantageously snaps onto and off of the outer cannula with only minimal or essentially no longitudinal force, in order to prevent pain and discomfort to the patient. The coupling connector is mounted on the proximal end of the inner cannula and includes an integral male adaptor, which communicates with the bore of the inner cannula, for receiving respiratory or anesthesia equipment. The connector and male cannula are designed to allow an adequate degree of rotational freedom of the connector relative to the outer cannula so that normal movement of the patient relative to the respiratory or anesthesia equipment is tolerated without causing any painful movement of the outer cannula. Furthermore, the nature of the coupling connection between the outer and inner cannulae is such that it provides for a secure attachment while permitting some longitudinal movement or "give" of the inner cannula with respect to the outer cannula.

Inner cannulae so constructed are completely interchangeable, and at the same time provide an air seal with the outer cannula without extending substantially beyond it. That is, each inner cannula possesses a certain minimum length which is sufficient to permit the tapered sealing surface at its distal end to engage the outer cannula (thereby forming the air seal and stop devices)

and to permit the coupling connector on its proximal end to snap onto the outer cannula. The stop device then serves to compensate for variations in length by preventing protrusion of the tip substantially beyond the outer cannula. Being secured at each end, the inner cannula further compensates for variations in length by virtue of its own flexibility and the longitudinal give permitted by the coupling connector. These features enable the inner cannulae of the present invention to be both dimensionally compatible and efficiently operative with any particular outer cannula.

Another important feature of the inner cannula of the present invention, which enhances its disposability, is the relative inexpense associated with the polymer materials and methods of manufacture from which it is constructed. For example, the inner cannulae can be quickly and easily produced in large quantities using an injection molding process. Alternatively, they can be extruded and then end-formed using a Radio Frequency (RF) di-electric heating process. Furthermore, dimensional tolerances are held close only in the distal area of the inner cannula to assure adequate sealing and stopping, since variations over its remaining length are offset as explained above. Additionally, due to their interchangeability, inner cannulae of the present invention need not be dimensionally customized to properly fit a particular outer cannula.

DETAILED DESCRIPTION OF THE INVENTION

Figure 1:
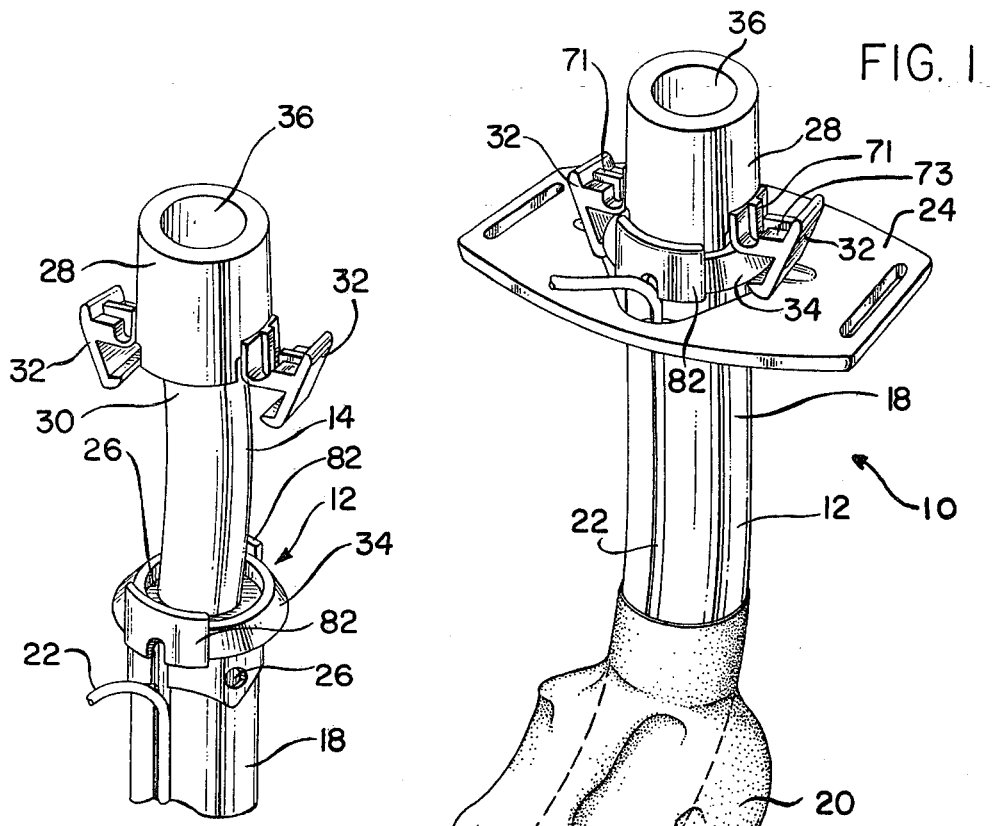
FIG. 1 is a perspective view of the tracheostomy tube of the present invention shown completely assembled.
Figure 2:
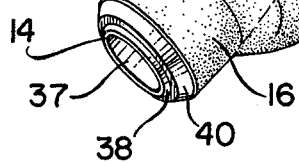
FIG. 2 is a partial perspective view of the tracheostomy tube with the inner cannula partially removed.

Referring initially to FIGS. 1 and 2, there is shown the tracheostomy tube 10 of the present invention, including an outer cannula 12 and a removable inner cannula 14, shown partially removed in FIG. 2. The cylindrical, arcuate outer cannula 12 is comprised of a distal end 16 for insertion into the trachea of the patient through an opening in the neck and a proximal end 18 remaining outside the trachea.

Shown attached to the tracheostomy tube 10 near its distal end 16 is an inflatable cuff 20 which, when inflated, provides an air tight seal between the tracheostomy tube 10 and the inner wall of the trachea. Such sealing cuffs are described in more detail and claimed in U.S. Pat. Nos. 3,659,612, and 3,693,624, assigned to Shiley, Inc. The cuff 20 is inflated by means of a flexible inflation tube 22 which extends into the cuff 20 from the proximal end 18 of the outer cannula 12. A swivel neck flange 24 located near the proximal end 18 of the outer cannula 12 is used to secure the tracheostomy tube 10 to the neck of the patient. The neck flange 24 is journaled in a pair of recessed openings 26 (FIG. 2) in the outer cannula 12 to permit a degree of rotational freedom of the flange 24 and the patient's neck with respect to the outer cannula 12, significantly decreasing the pain and discomfort that may be caused by the patient's normal bodily movements.

Figure 4:
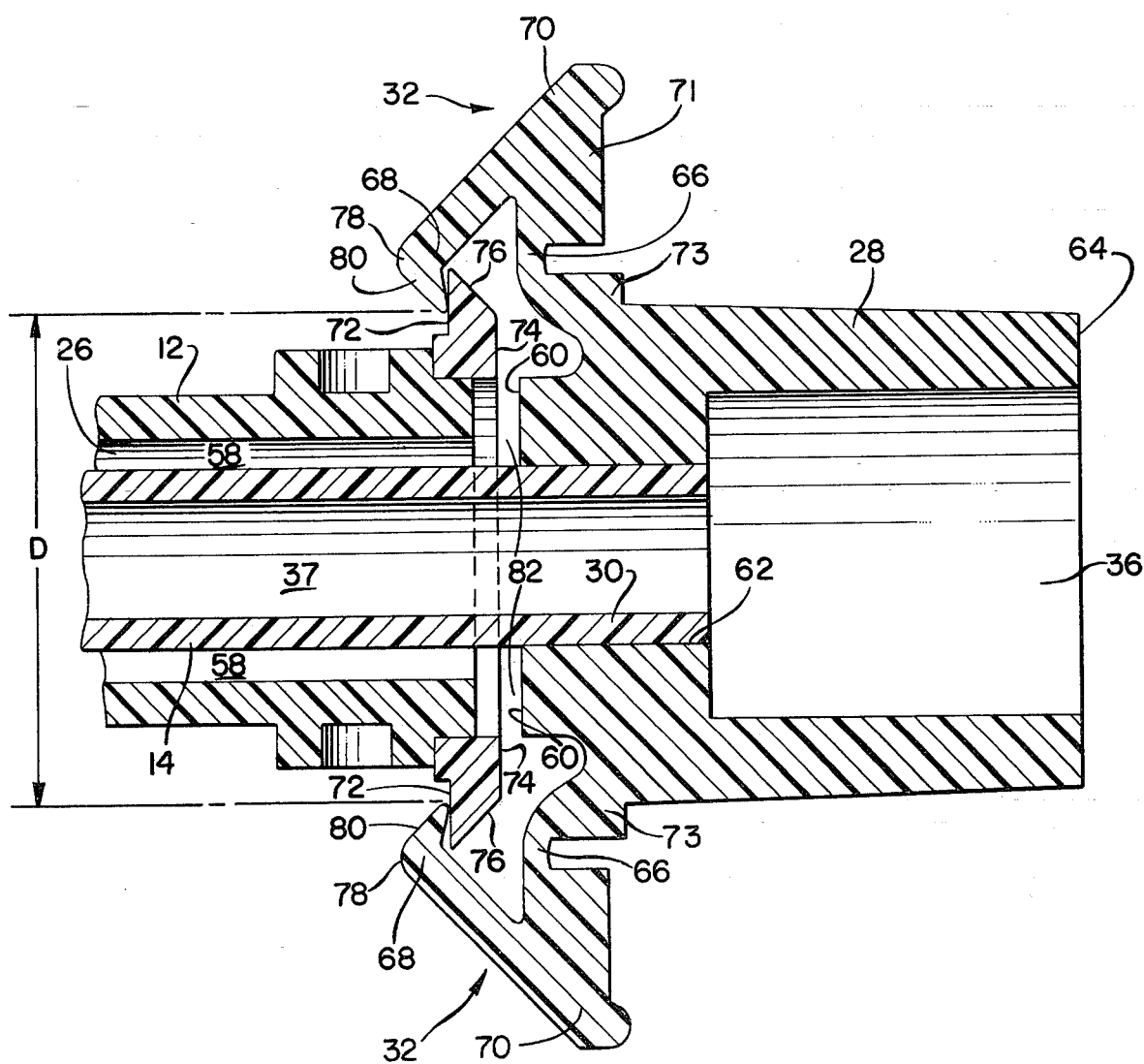
FIG. 4 is a partial sectional view taken through the coupling connector and the proximal end of the inner and outer cannulae.

The inner cannula 14 is inserted into the bore 26 of the outer cannula 12 and secured in place by means of a coupling connector 28 mounted on its proximal end 30, as shown in FIG. 2. The connector 28, which will be described in more detail in connection with FIG. 4, is provided with a pair of resilient lever arms 32 which engage an annular retaining collar 34 located on the proximal end 18 of the outer cannula 12. The proximal end of the coupling connector 28 is provided with an opening 36 for receiving anesthesia equipment or artificial respiratory equipment (not shown) to assist the patient's breathing. As clearly shown in FIG. 1, the inner cannula 14 runs the entire length of the outer cannula 12 so that its distal tip 38 is flush with or slightly beyond the tapered necked-down portion 40 of the distal end 16 of the outer cannula 12 and the connector 28 is securely releasably attached to the proximal end 18 of the outer cannula 12. Formed in the inner cannula 14 is a passageway 37 which communicates with the opening 36 in the connector 28 to permit air to flow into the trachea.

Figure 3:
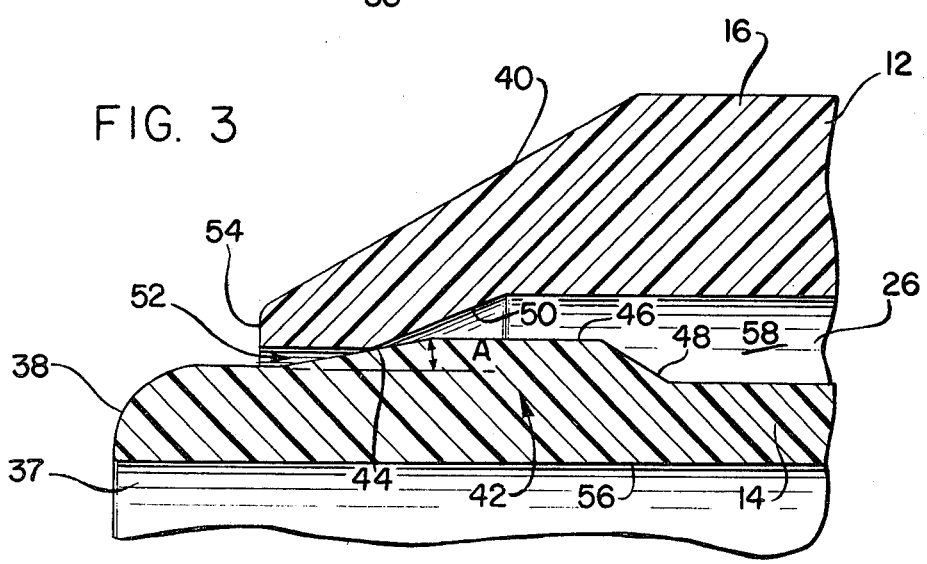
FIG. 3 is a partial sectional view taken through the distal end of the inner and outer cannulae.

FIG. 3 is a partial sectional view taken through the distal end of the tracheostomy tube 10 of the present invention. Located just behind the tip 38 of the inner cannula 14 is a raised annular section 42 comprised of, from front to rear, a tapered, forwardly facing sealing surface 44, a non-tapered surface 46, and a tapered rearwardly facing surface 48. The sealing surface 44 is frustro-conical in shape and engages the interior surface 50 of the necked-down portion 40 on the distal end 16 of the outer cannula 12 to form a tight air seal between the outer cannula 12 and inner cannula 14. This sealing surface 44 is sufficiently tapered so that at least one portion has an outer diameter which is greater than the inside diameter of the opening 52 of the outer cannula 12. Thus, only a slight axial force is required to wedge the sealing surface 44 of the inner cannula 14 into the opening 52 of the outer cannula 12 to form this air seal. Furthermore, it has been found that a sealing surface 44 having a slope A with respect to the horizontal of about 10-15 degrees is preferable, since within this range the inclination of the sealing surface 44 is sufficient to form a wedge-like seal with the necked-down portion 40 of the outer cannula 12, without creating an undesirably long sealing surface 44.

As clearly illustrated in FIG. 3, the engagement between the inner cannula 14 and the outer cannula 12 also serves as a stop device to prevent the tip 38 of the inner cannula 14 from extending substantially beyond the very end 54 of the outer cannula 12. Moreover, the sloping interior surface 50 of the necked-down portion 40 of the outer cannula 12 cooperates to form this stop device since it presents a large, relatively rigid obstacle to the raised portion 42 on the inner cannula 14 which prohibits substantial protrusion of the tip 38. Furthermore, the location and length of the sealing surface 44 on the inner cannula 14 and the size of opening 52 on the outer cannula 12, which together form the air seal and stop devices of the present invention, are such that the tip 38 will be flush with the end 54 of the outer cannula if the interior surface 50 contacts the sealing surface 44 near its lower edge. If, on the other hand, the interior surface 50 contacts the upper edge of the sealing surface 44, the tip 38 will extend only slightly, e.g. about 0.050 inches, beyond the end 54 of the outer cannula. Thus, the stop device of the present invention advantageously regulates the position of the tip 38 within this narrow range, thereby compensating for variations in overall length among the present inner cannulae.

This minimal amount of possible extension is not sufficient to cause injury to the patient's trachea. The trachea is further protected by the rounded shape of the tip 38 of the inner cannula 14 and by the soft, biologically compatable polymer material from which it is constructed. Moreover, the length of the inner cannula 14 is such that the tip 38 does not terminate within the opening 52 of the outer cannula 12. This construction ensures the proper elimination of obstructions in the passageway 37 of the tracheostomy tube 10 upon removal of the disposable inner cannula 14. In the unlikely event that the raised portion 42 on the inner cannula 14 is forced beyond the end 54 of the outer cannula 12, the rear tapered surface 48 of the raised portion 42 facilitates removal of the inner cannula 14 from the opening 52 in the outer cannula 12.

As mentioned above, the inner cannula 14 of the present invention can be constructed from a soft, flexible, polymer material, preferably a non-toxic polyvinyl chloride having a Shore A hardness of about 85. However, any other soft, biologically safe, elastomeric material having a Shore A hardness of 90 or less is also suitable. Moreover, the inner cannula 14 can be inexpensively manufactured using plastic injection molding techniques or can be made in a two part process including an extrusion step followed by the di-electric end forming of the tip 38 and raised portion 42.

As is well known, shrinkage is a common problem experienced in the molding and forming of plastics, making dimensional tolerances difficult to hold. In the present invention, however, dimensional tolerances advantageously need be held closely only at the distal end of the inner cannula 14, where the critical tip 38 and sealing surface 44 are located, rather than over the entire length of the inner cannula. Furthermore, any dimensional inaccuracies in this area and any variations in length over the remainder of the inner cannula 14 are offset by the tracheostomy tube 10 of the present invention, as described below in more detail. Furthermore, there is no customized, cutting to length of the inner cannula 14 with respect to a particular outer cannula 12, since inner cannulae of the present invention are interchangeable. Thus, the inner cannula 14 of the present invention can be inexpensively manufactured, making its disposability economically practical.

Referring again to FIG. 3, either of the above-mentioned methods of manufacturing the inner cannula 14 produce a passageway 37 having a completely smooth interior surface 56. This feature reduces the frictional forces exerted on air and anesthetic gas delivered to the patient through the tracheostomy tube 10, thereby enhancing its efficiency. Additionally, this smooth inner surface 56 provides for an essentially frictionless flow of bodily secretions which may enter the inner cannula 14, thus reducing the amount of such secretions which adhere to it and obstruct its passageway 56. Thus, the present inner cannula 14, to a degree, is self-cleaning and must be replaced only infrequently.

As shown in FIG. 3 the outer diameter of the inner cannula 14 at points proximal to the raised portion 42 is sufficiently less than the inner diameter of the outer cannula 12 at corresponding locations to form a gap or space 58 within the bore 26 of the outer cannula 12. This space 58 permits the flexible inner cannula 14 to bend, if necessary, within the outer cannula 12, allowing tracheostomy tube 10 of the present invention to further compensate for variations in length of the inner cannula 14 and to provide for its interchangeability.

FIG. 4 is a sectional view taken through the proximal end of the present tracheostomy tube 10, illustrating the outer cannula 12, the inner cannula 14 removably installed within the bore 26 of the outer cannula 12, and the coupling connector 28 mounted on the proximal end 30 of the inner cannula 14 for attaching it to the outer cannula 12. The connector 28 has a distal face 60 with an opening 62 to receive the inner cannula 14. The proximal face 64 of the connector 28 is provided with a large opening 36 adapted to receive a conduit (not shown) from respiratory or anesthesia equipment which fits over the proximal end of the connector 28. The connector 28 is preferably constructed from copolyester or polypropylene material and then bonded to the inner cannula 14 by a solvent or other suitable means. Furthermore, the connector 28 can be inexpensively manufactured using injection molding techniques.

Integrally formed on opposite sides of the coupling connector 28 are a pair of lever arms 32 which are biased forwardly or toward one another by arcuate, resilient hinges 66. In their relaxed state, these hinges 66 cause the lever arms 32 to assume the position shown in FIG. 4. The lever arms 32 have locking ends 68, which are separated by a distance D, and handle ends 70. Each locking end 68 engages the distal face 72 of the retaining collar 34, which is mounted on the extreme proximal end 18 of the outer cannula 12, to lock the connector 28 and inner cannula 14 assembly in place. The handle end 70 provides a finger location for the manual manipulation of the lever arms 32. The retaining collar 34 is also characterized by a proximal face 74, which is parallel with the distal face 60 of the connector 28, and by a tapered peripheral surface 76 which facilitates attachment of the connector 28 to the outer cannula 12.

In operation, the coupling connector 28 of the present invention permits the inner cannula 14 to be easily and securely attached to the outer cannula 12 in a single axial, non-rotational movement. The tip 38 of the inner cannula 14 is first inserted into the bore 26 of the outer cannula 12 and advanced until the locking ends 68 of the lever arms 32 engage the tapered periphery 76 of the retaining collar 34. Only slight axial force is then necessary to cause the lever arms 32 to be flexed backward, gradually increasing the distance D between the locking ends 68 as they advance along the collar periphery 76. When the distance D is greater than the outside diameter of the collar 34, the hinges 66 snap the locking ends 68 toward one another in locking engagement with the distal face 72 of the retaining collar 34.

As shown in FIG. 4, the connector/inner cannula assembly is locked to the outer cannula since the distance D between locking ends 68 of the lever arms 32, in their relaxed state, is less than the greatest outside diameter of the retaining collar 34. Attachment of the connector 28 to the outer cannula 12 is facilitated by the rounded leading edges 78 and including forward surface 80 on the locking ends 68 of the lever arms 32. This forward surface 80, which is inclined at approximately the same angle as the tapered periphery 76 of the retaining collar 34, reduces the amount of axial force necessary to cause the locking ends 68 to separate as they are advanced along the collar periphery 76.

Alternatively, the connector 28 can be attached to the outer cannula 12 with virtually no axial forces being exerted on the tracheostomy tube 10. In this method, the inner cannula 14 is inserted into the outer cannula 12 and advanced, as before, until the locking ends 68 of the lever arms 32 are positioned close to the tapered periphery 76 of the retaining collar 34. The locking ends 68 are then manually spread apart by exerting an inward force from the fingers on the handle ends 70 of the lever arms 32 until the locking ends 68 are separated by a distance D greater than the diameter of the collar 34. The connector 28 is then advanced slightly and the handle ends 70 released, permitting the hinges 66 to bias the locking ends 68 together in locking engagement with the distal face 72 of the retaining collar 34. The connector 28 of the present invention is unlocked and the inner cannula 14 removed from the outer cannula 12 by reversing these simple steps.

In utilizing this manual method for locking or unlocking the connector 28, the hinges 66 are protected from damage due to backwards hyperextension by ribs 71 (also shown in FIG. 1) located on the back side of the handle ends 70 of the lever arms 32. These ribs 71 contact stop blocks 73 to prevent the lever arms 32 from bending too far backwards during attachment or removal of the connector 28.

Thus, inner cannula 14 of the present invention is easily attached to and removed from the outer cannula 12 with exertion of little or no longitudinal force, thereby preventing pain and discomfort to the patient. Furthermore, once attached to the outer cannula 12, the coupling connector 28 of the present invention permits a degree of rotational freedom of the inner cannula 14 with respect to the outer cannula 12 so that the normal movement of the patient relative to a respiratory or anesthesia conduit attached over the opening 36 in the proximal end 64 of the connector 28 will also not cause pain or discomfort. This rotational freedom is derived from the flexibility of the inner cannula 14 which, even though substantially fixed with respect to the outer cannula 12 at its distal end, absorbs the torsional forces exerted upon it by the rotation of the connector 28 at its proximal end 30. This rotational freedom is limited, however, by a pair of spaced tabs 82 (shown in FIGS. 1 and 2) which protect the inflation tube 22 from damage by contact with either of the lever arms 32.

A significant feature of the coupling connector 28 of the present invention, which promotes the interchangeability and disposability of the inner cannula 14, is that it serves to securely attach the inner cannula 14 to the outer cannula 12 while providing for a small gap 82 between the distal face 60 of the connector 28 and the proximal face 74 of the retaining collar 34. This gap 82 permits a degree of axial movement of the inner cannula 14 with respect to the outer cannula 12 in order to compensate for variations in the length among inner cannulae of the present invention, due for example to shrinkage during manufacture. Another important feature in this regard is the flexibility of the inner cannula 14 which permits it to bend within the gap 58 (shown in FIGS. 3 and 4) between the inner cannula 14 and the outer cannula 12.

Thus, the inner cannula 14 of the present invention need only possess a certain minimum length sufficient to permit some portion of its sealing surface 44 to wedge against the interior surface 50 of the necked down portion 40 of the outer cannula 12, thereby forming the air seal shown in FIG. 3, and to permit the locking ends 68 of the lever arms 32 to engage the distal face 72 of the retaining collar 34, as shown in FIG. 4. Beyond this minimum length, variations in length are offset by the axial give in the coupling connector 28 and by the bending flexibility of the inner cannula 14 itself. Furthermore, the tip 38 of the inner cannula 14 is prevented from extending substantially beyond the end 54 of the outer cannula 12, as explained above, further compensating for lengthwise variations.

This ability of the present tracheostomy tube to compensate for dimensional differences among inner cannulae provides for the interchangeability and disposability of the inner cannula 14 of the present invention. Furthermore, as described above, these inner cannulae are sufficiently economical in terms of material and manufacturing cost to make their disposability practical, thus avoiding the problems and cost of sterilization.

What is claimed is:

1. A tracheostomy tube for insertion into a patient's trachea through an opening in the neck to assist breathing, said tube being adapted to use with disposable inner cannulae, comprising:

an outer cannula having a distal end for insertion within said trachea and a proximal end remaining outside said trachea, said distal end having a reduced diameter portion;

a disposable inner cannula having approximately at least the same length or longer length as said outer cannula removably inserted into said outer cannula, said disposable inner cannula having a tip at its distal end comprising an annular raised portion with an annular tapered surface sloping toward said tip, means for stationarily securing said inner cannula to said outer cannula; and said tapered surface on said inner cannula abutting against said reduced diameter portion on said outer cannula upon insertion of said inner cannula into said outer cannula thereby providing means proximal the distal end of said disposable inner cannula and said outer cannula for (i) forming a gas seal between said disposable inner cannula and said outer cannula for preventing leakage of either incoming or expelling gas and (ii) compensating for dimensional variations in said disposable inner cannula by insuring that the distal tip of said inner cannula is flush with or extends only slightly beyond the end of the outer cannula.

2. The tracheostomy tube of claim 1 wherein said tapered surface is frustro-conical in shape.

3. A tracheostomy tube for insertion into a patient's trachea through an opening in the neck to assist breathing, said tube being adapted for use with disposable inner cannulae, comprising:

an outer cannula having a distal end for insertion within said trachea and a proximal end remaining outside said trachea;

a disposable inner cannula having approximately at least the same length or longer as said outer cannula removably inserted into said outer cannula, said disposable inner cannula having a tip at its distal end, means for stationarily securing said inner cannula to said outer cannula;

means proximal the distal end of said disposable inner cannula and said outer cannula for (i) forming a gas seal between said disposable inner cannula and said outer cannula for preventing leakage of either incoming or expelling gas and (ii) compensating for demensional variations in said disposable inner cannula by insuring that the distal tip of said inner cannula is flush with or extends only slightly beyond the end of the outer cannula, said means proximal said distal end comprising an annular raised portion on said cannula having an annular tapered surface which slopes toward said tip and a reduced diameter portion on said outer cannula near the distal end of said outer cannula wherein said tapered surface abutts said reduced diameter portion when said cannula is inserted into said cannula.

4. A tracheostomy tube for insertion into a patient's trachea through an opening in the neck, comprising:

an outer cannula having a reduced diameter portion near its distal end; and an inner cannula having approximately at least the same length or longer length as said outer cannula removeably inserted into said outer cannula, means for stationarily securing said inner cannula to said outer cannula, said inner cannula having an annular raised portion near its distal end adjacent said reduced diameter portion of said outer cannula with an annular tapered surface sloping toward its distal tip, said tapered surface on said inner cannula abutting against said reduced diameter portion on said outer cannula when said inner cannula is inserted into said outer cannula to form gas seal means for preventing leakage of gas from said tracheostomy tube and for facilitating said patient's breathing.

* * * * *